United States Patent
Li et al.

(10) Patent No.: US 10,325,065 B2
(45) Date of Patent: Jun. 18, 2019

(54) METHOD AND SYSTEM FOR CREATING PATIENT-SPECIFIC INSTRUMENTATION FOR CHONDRAL GRAFT TRANSFER

(71) Applicant: ZIMMER, INC., Warsaw, IN (US)

(72) Inventors: Jia Li, Warsaw, IN (US); David Hatfield, Warsaw, IN (US)

(73) Assignee: ZIMMER, INC., Warsaw, IN (US)

( * ) Notice: Subject to any disclaimer, the term of this patent is extended or adjusted under 35 U.S.C. 154(b) by 630 days.

(21) Appl. No.: 13/749,009

(22) Filed: Jan. 24, 2013

(65) Prior Publication Data

US 2013/0191085 A1 Jul. 25, 2013

Related U.S. Application Data

(60) Provisional application No. 61/590,157, filed on Jan. 24, 2012.

(51) Int. Cl.
G06F 17/50 (2006.01)
G06F 19/00 (2018.01)
(Continued)

(52) U.S. Cl.
CPC .......... *G06F 19/00* (2013.01); *A61B 17/1604* (2013.01); *A61B 17/1635* (2013.01);
(Continued)

(58) Field of Classification Search
None
See application file for complete search history.

(56) References Cited

U.S. PATENT DOCUMENTS 4,841,975 A 6/1989 Woolson
5,098,383 A 3/1992 Hemmy et al.
(Continued)

FOREIGN PATENT DOCUMENTS

AU 2004293091 A1 6/2005
AU 2004293104 A1 6/2005
(Continued)

OTHER PUBLICATIONS

Taylor et al, "Computer-Integrated Surgery, Technology and Clinical Applications", The MIT Press, Cambridge, MA, London, UK, pp. 451-463.
(Continued)

*Primary Examiner* — Aniss Chad
*Assistant Examiner* — Cuong V Luu
(74) *Attorney, Agent, or Firm* — Norton Rose Fulbright Canada LLP

(57) ABSTRACT

A system for creating a patient-specific instrument model for chondral graft plugging comprises a bone model generator for producing a bone/cartilage model of an articular region of a bone from images thereof. A defect geometry identifier identifies a graft geometry from a defect region of said bone/cartilage model. A donor locator locates an autograft at a donor site or identifies an allograft from a database, using said bone/cartilage model and the graft geometry. A patient-specific instrument model generator creates a model of a graft-plugging patient-specific instrument from said bone/cartilage model, and the graft geometry, the graft-plugging patient-specific instrument model comprising a bone/cartilage interface surface shaped as a function of the bone/cartilage model for the at least one graft-plugging patient-specific instrument to be selectively positioned on the bone/cartilage to pose the autograft or the allograft at the defect region.

20 Claims, 3 Drawing Sheets

(51) Int. Cl.
  *A61B 17/3205*  (2006.01)
  *A61B 17/16*  (2006.01)
  *G16H 50/50*  (2018.01)
  *A61B 17/00*  (2006.01)
  *A61B 17/32*  (2006.01)
  *A61B 17/56*  (2006.01)
  *A61B 34/10*  (2016.01)

(52) U.S. Cl.
  CPC ....... *A61B 17/32053* (2013.01); *G16H 50/50* (2018.01); *A61B 2017/00969* (2013.01); *A61B 2017/320052* (2013.01); *A61B 2017/320064* (2013.01); *A61B 2017/568* (2013.01); *A61B 2034/108* (2016.02); *F04C 2270/041* (2013.01)

(56) References Cited

U.S. PATENT DOCUMENTS

| | | |
|---|---|---|
| 5,490,854 A | 2/1996 | Fisher et al. |
| 5,768,134 A | 6/1998 | Swaelens et al. |
| 5,871,018 A | 2/1999 | Delp et al. |
| 5,916,219 A | 6/1999 | Matsuno et al. |
| 7,357,057 B2 | 4/2008 | Chiang |
| 7,468,075 B2 | 12/2008 | Lang et al. |
| 7,510,557 B1 | 3/2009 | Bonutti |
| 7,534,263 B2 | 5/2009 | Burdulis |
| 7,618,451 B2 | 11/2009 | Berez et al. |
| 7,634,119 B2 | 12/2009 | Tsougarakis et al. |
| 7,717,956 B2 | 5/2010 | Lang |
| 7,796,791 B2 | 9/2010 | Tsougarakis et al. |
| 7,799,077 B2 | 9/2010 | Lang et al. |
| 7,806,896 B1 | 10/2010 | Bonutti |
| 7,806,897 B1 | 10/2010 | Bonutti |
| 7,967,868 B2 | 6/2011 | White et al. |
| 7,981,158 B2 | 7/2011 | Fitz et al. |
| 8,062,302 B2 | 11/2011 | Lang et al. |
| 8,066,708 B2 | 11/2011 | Lang et al. |
| 8,070,752 B2 | 12/2011 | Metzger et al. |
| 8,077,950 B2 | 12/2011 | Tsougarakis et al. |
| 8,083,745 B2 | 12/2011 | Lang et al. |
| 8,092,465 B2 | 1/2012 | Metzger et al. |
| 8,094,900 B2 | 1/2012 | Steines et al. |
| 8,105,330 B2 | 1/2012 | Fitz et al. |
| 8,122,582 B2 | 2/2012 | Burdulis, Jr. et al. |
| 8,133,234 B2 | 3/2012 | Meridew et al. |
| 8,160,345 B2 | 4/2012 | Pavlovskaia et al. |
| 8,175,683 B2 | 5/2012 | Roose |
| 8,221,430 B2 | 7/2012 | Park et al. |
| 8,234,097 B2 | 7/2012 | Steines et al. |
| 8,241,293 B2 | 8/2012 | Stone et al. |
| 8,282,646 B2 | 10/2012 | Schoenefeld et al. |
| 8,298,237 B2 | 10/2012 | Schoenefeld |
| 8,337,501 B2 | 12/2012 | Fitz et al. |
| 8,337,507 B2 | 12/2012 | Lang et al. |
| 8,343,218 B2 | 1/2013 | Lang et al. |
| 8,366,771 B2 | 2/2013 | Burdulis et al. |
| 8,377,129 B2 | 2/2013 | Fitz et al. |
| 8,439,926 B2 | 5/2013 | Bojarski et al. |
| 8,444,651 B2 | 5/2013 | Kunz |
| 8,460,304 B2 | 6/2013 | Fitz et al. |
| 8,480,754 B2 | 7/2013 | Bojarski et al. |
| 8,500,740 B2 | 8/2013 | Bojarski et al. |
| 8,529,568 B2 | 9/2013 | Bouadi |
| 8,529,630 B2 | 9/2013 | Bojarski |
| 8,585,708 B2 | 9/2013 | Fitz et al. |
| 8,545,569 B2 | 10/2013 | Fitz et al. |
| 8,551,099 B2 | 10/2013 | Lang |
| 8,551,102 B2 | 10/2013 | Fitz et al. |
| 8,551,103 B2 | 10/2013 | Fitz et al. |
| 8,551,169 B2 | 10/2013 | Fitz et al. |
| 8,556,906 B2 | 10/2013 | Fitz et al. |
| 8,556,907 B2 | 10/2013 | Fitz et al. |
| 8,556,971 B2 | 10/2013 | Lang |
| 8,556,983 B2 | 10/2013 | Bojarski et al. |
| 8,561,278 B2 | 10/2013 | Fitz et al. |
| 8,562,611 B2 | 10/2013 | Fitz et al. |
| 8,562,618 B2 | 10/2013 | Fitz et al. |
| 8,568,479 B2 | 10/2013 | Fitz et al. |
| 8,568,480 B2 | 10/2013 | Fitz et al. |
| 8,617,172 B2 | 12/2013 | Fitz et al. |
| 8,617,242 B2 | 12/2013 | Philipp |
| 8,623,026 B2 | 1/2014 | Wong et al. |
| 8,634,617 B2 | 1/2014 | Tsougarakis et al. |
| 8,638,998 B2 | 1/2014 | Steines et al. |
| 8,641,716 B2 | 2/2014 | Fitz et al. |
| 8,657,827 B2 | 2/2014 | Fitz et al. |
| 8,682,052 B2 | 3/2014 | Fitz et al. |
| 2002/0157676 A1 | 10/2002 | Schmieding |
| 2003/0055502 A1 | 3/2003 | Lang et al. |
| 2003/0216669 A1 | 11/2003 | Lang et al. |
| 2004/0133276 A1 | 7/2004 | Lang et al. |
| 2004/0138754 A1 | 7/2004 | Lang et al. |
| 2004/0147927 A1 | 7/2004 | Tsougarakis et al. |
| 2004/0153079 A1 | 8/2004 | Tsougarakis et al. |
| 2004/0204644 A1 | 10/2004 | Tsougarakis et al. |
| 2004/0204760 A1 | 10/2004 | Fitz et al. |
| 2004/0236424 A1 | 11/2004 | Berez et al. |
| 2005/0234461 A1 | 10/2005 | Burdulis et al. |
| 2005/0267584 A1 | 12/2005 | Burdulis et al. |
| 2006/0111722 A1 | 5/2006 | Bouadi |
| 2007/0083266 A1 | 4/2007 | Lang |
| 2007/0093896 A1 | 4/2007 | Malinin |
| 2007/0100462 A1 | 5/2007 | Lang et al. |
| 2007/0156171 A1 | 7/2007 | Lang et al. |
| 2007/0157783 A1 | 7/2007 | Chiang |
| 2007/0198022 A1 | 8/2007 | Lang et al. |
| 2007/0226986 A1 | 10/2007 | Park et al. |
| 2007/0233141 A1 | 10/2007 | Park et al. |
| 2007/0233269 A1 | 10/2007 | Steines et al. |
| 2007/0250169 A1 | 10/2007 | Lang |
| 2008/0114370 A1 | 5/2008 | Schoenefeld |
| 2008/0147072 A1 | 6/2008 | Park et al. |
| 2008/0161815 A1 | 7/2008 | Schoenefeld et al. |
| 2008/0195216 A1 | 8/2008 | Philipp |
| 2008/0243127 A1 | 10/2008 | Lang et al. |
| 2008/0275452 A1 | 11/2008 | Lang et al. |
| 2008/0281328 A1 | 11/2008 | Lang et al. |
| 2008/0281329 A1 | 11/2008 | Fitz et al. |
| 2008/0281426 A1 | 11/2008 | Fitz et al. |
| 2008/0287954 A1 | 11/2008 | Kunz et al. |
| 2009/0024131 A1 | 1/2009 | Metzgu et al. |
| 2009/0088753 A1 | 4/2009 | Aram et al. |
| 2009/0088754 A1 | 4/2009 | Aker et al. |
| 2009/0088755 A1 | 4/2009 | Aker et al. |
| 2009/0088758 A1 | 4/2009 | Bennett |
| 2009/0088759 A1 | 4/2009 | Aram et al. |
| 2009/0088760 A1 | 4/2009 | Aram et al. |
| 2009/0088761 A1 | 4/2009 | Roose et al. |
| 2009/0088763 A1 | 4/2009 | Aram et al. |
| 2009/0093816 A1 | 4/2009 | Roose et al. |
| 2009/0099567 A1 | 4/2009 | Zajac |
| 2009/0110498 A1 | 4/2009 | Park et al. |
| 2009/0131941 A1 | 5/2009 | Park et al. |
| 2009/0131942 A1 | 5/2009 | Aker et al. |
| 2009/0138020 A1 | 5/2009 | Park et al. |
| 2009/0157083 A1 | 6/2009 | Park et al. |
| 2009/0209962 A1* | 8/2009 | Jamali ............... A61B 17/1635 606/81 |
| 2009/0222014 A1 | 9/2009 | Bojarksi et al. |
| 2009/0222016 A1 | 9/2009 | Park et al. |
| 2009/0222103 A1 | 9/2009 | Fitz et al. |
| 2009/0226068 A1 | 9/2009 | Fitz et al. |
| 2009/0228113 A1 | 9/2009 | Lang et al. |
| 2009/0254093 A1 | 10/2009 | White et al. |
| 2009/0270868 A1 | 10/2009 | Park et al. |
| 2009/0276045 A1 | 11/2009 | Lang |
| 2009/0306676 A1 | 12/2009 | Lang et al. |
| 2009/0307893 A1 | 12/2009 | Burdulis, Jr. et al. |
| 2009/0312805 A1 | 12/2009 | Lang et al. |
| 2010/0023015 A1 | 1/2010 | Park |
| 2010/0042105 A1 | 2/2010 | Park et al. |
| 2010/0049195 A1 | 2/2010 | Park et al. |
| 2010/0054572 A1 | 3/2010 | Tsougarakis et al. |
| 2010/0082035 A1 | 4/2010 | Keefer |

(56) References Cited

U.S. PATENT DOCUMENTS

| | | |
|---|---|---|
| 2010/0087829 A1 | 4/2010 | Metzger et al. |
| 2010/0152741 A1 | 6/2010 | Park et al. |
| 2010/0152782 A1 | 6/2010 | Stone et al. |
| 2010/0160917 A1 | 6/2010 | Fitz et al. |
| 2010/0168754 A1 | 7/2010 | Fitz et al. |
| 2010/0174376 A1 | 7/2010 | Lang et al. |
| 2010/0185202 A1 | 7/2010 | Lester et al. |
| 2010/0191244 A1 | 7/2010 | White et al. |
| 2010/0212138 A1 | 8/2010 | Carroll et al. |
| 2010/0217270 A1 | 8/2010 | Polinski et al. |
| 2010/0217338 A1 | 8/2010 | Carroll et al. |
| 2010/0228257 A1 | 9/2010 | Bonutti |
| 2010/0234849 A1 | 9/2010 | Bouadi |
| 2010/0256479 A1 | 10/2010 | Park et al. |
| 2010/0262150 A1 | 10/2010 | Lian |
| 2010/0274534 A1 | 10/2010 | Steines et al. |
| 2010/0281678 A1 | 11/2010 | Burdulis, Jr. et al. |
| 2010/0286700 A1 | 11/2010 | Snider et al. |
| 2010/0298894 A1* | 11/2010 | Bojarski et al. ... A61B 17/1764 606/86 R |
| 2010/0303313 A1 | 12/2010 | Lang et al. |
| 2010/0303317 A1 | 12/2010 | Tsougarakis et al. |
| 2010/0303324 A1 | 12/2010 | Lang et al. |
| 2010/0305573 A1 | 12/2010 | Fitz et al. |
| 2010/0305574 A1 | 12/2010 | Fitz et al. |
| 2010/0305708 A1 | 12/2010 | Lang et al. |
| 2010/0305907 A1 | 12/2010 | Fitz et al. |
| 2010/0329530 A1 | 12/2010 | Lang et al. |
| 2011/0015636 A1 | 1/2011 | Katrana et al. |
| 2011/0015637 A1 | 1/2011 | De Smedt et al. |
| 2011/0015639 A1 | 1/2011 | Metzger et al. |
| 2011/0029091 A1 | 2/2011 | Bojarski et al. |
| 2011/0029093 A1 | 2/2011 | Bojarski et al. |
| 2011/0040168 A1 | 2/2011 | Arnaud et al. |
| 2011/0054478 A1 | 3/2011 | Vanasse et al. |
| 2011/0060341 A1 | 3/2011 | Angibaud et al. |
| 2011/0066193 A1 | 3/2011 | Lang et al. |
| 2011/0066245 A1 | 3/2011 | Lang et al. |
| 2011/0071533 A1 | 3/2011 | Metzger et al. |
| 2011/0071581 A1 | 3/2011 | Lang et al. |
| 2011/0071645 A1 | 3/2011 | Bojarski et al. |
| 2011/0071802 A1 | 3/2011 | Bojarski et al. |
| 2011/0087332 A1 | 4/2011 | Bojarski et al. |
| 2011/0092977 A1 | 4/2011 | Salehi et al. |
| 2011/0093108 A1 | 4/2011 | Ashby et al. |
| 2011/0106093 A1 | 5/2011 | Romano et al. |
| 2011/0125003 A1* | 5/2011 | Reach ............ A61F 2/4657 600/407 |
| 2011/0144760 A1 | 6/2011 | Wong et al. |
| 2011/0160736 A1 | 6/2011 | Meridew et al. |
| 2011/0160867 A1 | 6/2011 | Meridew et al. |
| 2011/0166578 A1 | 7/2011 | Stone et al. |
| 2011/0172672 A1 | 7/2011 | Dubeau et al. |
| 2011/0184419 A1 | 7/2011 | Meridew et al. |
| 2011/0196377 A1 | 8/2011 | Hodorek et al. |
| 2011/0213368 A1 | 9/2011 | Fitz et al. |
| 2011/0213373 A1 | 9/2011 | Fitz et al. |
| 2011/0213374 A1 | 9/2011 | Fitz et al. |
| 2011/0213376 A1 | 9/2011 | Maxson et al. |
| 2011/0213377 A1 | 9/2011 | Lang et al. |
| 2011/0213427 A1 | 9/2011 | Fitz et al. |
| 2011/0213428 A1 | 9/2011 | Fitz et al. |
| 2011/0213429 A1 | 9/2011 | Lang et al. |
| 2011/0213430 A1 | 9/2011 | Lang et al. |
| 2011/0213431 A1 | 9/2011 | Fitz et al. |
| 2011/0214279 A1 | 9/2011 | Park et al. |
| 2011/0218539 A1 | 9/2011 | Fitz et al. |
| 2011/0218545 A1 | 9/2011 | Catanzarite et al. |
| 2011/0218584 A1 | 9/2011 | Fitz et al. |
| 2011/0224674 A1 | 9/2011 | White et al. |
| 2011/0230888 A1 | 9/2011 | Lang et al. |
| 2011/0238073 A1 | 9/2011 | Lang et al. |
| 2011/0245835 A1 | 10/2011 | Dodds et al. |
| 2011/0266265 A1 | 11/2011 | Lang |
| 2011/0295329 A1 | 12/2011 | Fitz et al. |
| 2011/0295378 A1* | 12/2011 | Bojarski ............ A61F 2/30942 623/20.35 |
| 2011/0313423 A1 | 12/2011 | Lang et al. |
| 2011/0313424 A1 | 12/2011 | Bono et al. |
| 2011/0319745 A1* | 12/2011 | Frey ............ A61B 17/15 600/407 |
| 2011/0319897 A1 | 12/2011 | Lang et al. |
| 2011/0319900 A1 | 12/2011 | Lang et al. |
| 2012/0010711 A1 | 1/2012 | Antonyshyn et al. |
| 2012/0029520 A1 | 2/2012 | Lang et al. |
| 2012/0041445 A1 | 2/2012 | Roose et al. |
| 2012/0041446 A1 | 2/2012 | Wong et al. |
| 2012/0065640 A1 | 3/2012 | Metzger et al. |
| 2012/0066892 A1 | 3/2012 | Lang et al. |
| 2012/0071881 A1 | 3/2012 | Lang et al. |
| 2012/0071882 A1 | 3/2012 | Lang et al. |
| 2012/0071883 A1 | 3/2012 | Lang et al. |
| 2012/0072185 A1 | 3/2012 | Lang et al. |
| 2012/0078254 A1 | 3/2012 | Ashby et al. |
| 2012/0078258 A1 | 3/2012 | Lo et al. |
| 2012/0078259 A1* | 3/2012 | Meridew ............ A61B 17/1746 606/87 |
| 2012/0093377 A1 | 4/2012 | Tsougarakis et al. |
| 2012/0101503 A1 | 4/2012 | Lang et al. |
| 2012/0109138 A1 | 5/2012 | Meridew et al. |
| 2012/0116203 A1 | 5/2012 | Vancraen et al. |
| 2012/0116562 A1 | 5/2012 | Agnihotri et al. |
| 2012/0123422 A1 | 5/2012 | Agnihotri et al. |
| 2012/0123423 A1 | 5/2012 | Fryman |
| 2012/0130382 A1 | 5/2012 | Iannotti et al. |
| 2012/0130687 A1 | 5/2012 | Otto et al. |
| 2012/0141034 A1 | 6/2012 | Iannotti et al. |
| 2012/0143197 A1 | 6/2012 | Lang et al. |
| 2012/0150030 A1* | 6/2012 | Reach, Jr. ............ A61B 17/1604 600/427 |
| 2012/0151730 A1 | 6/2012 | Fitz et al. |
| 2012/0158001 A1 | 6/2012 | Burdulis, Jr. et al. |
| 2012/0165820 A1 | 6/2012 | De Smedt et al. |
| 2012/0172884 A1 | 7/2012 | Zheng et al. |
| 2012/0191205 A1 | 7/2012 | Bojarski et al. |
| 2012/0191420 A1 | 7/2012 | Bojarski et al. |
| 2012/0192401 A1 | 8/2012 | Pavlovskaia et al. |
| 2012/0197260 A1 | 8/2012 | Fitz et al. |
| 2012/0197408 A1 | 8/2012 | Lang et al. |
| 2012/0201440 A1 | 8/2012 | Steines et al. |
| 2012/0209276 A1 | 8/2012 | Schuster |
| 2012/0209394 A1 | 8/2012 | Bojarski et al. |
| 2012/0215226 A1 | 8/2012 | Bonutti |
| 2012/0221008 A1 | 8/2012 | Carroll et al. |
| 2012/0226283 A1 | 9/2012 | Meridew et al. |
| 2012/0232669 A1 | 9/2012 | Bojarski et al. |
| 2012/0232670 A1 | 9/2012 | Bojarski et al. |
| 2012/0232671 A1 | 9/2012 | Bojarski |
| 2012/0239045 A1 | 9/2012 | Li |
| 2012/0245647 A1 | 9/2012 | Kunz et al. |
| 2012/0245699 A1 | 9/2012 | Lang et al. |
| 2012/0265208 A1 | 10/2012 | Smith |
| 2012/0271366 A1 | 10/2012 | Katrana et al. |
| 2012/0276509 A1 | 11/2012 | Iannotti et al. |
| 2012/0277751 A1 | 11/2012 | Catanzarite et al. |
| 2012/0289966 A1 | 11/2012 | Fitz et al. |
| 2012/0296337 A1 | 11/2012 | Fitz et al. |
| 2013/0006250 A1* | 1/2013 | Metzger ............ A61B 17/155 606/87 |
| 2013/0018379 A1 | 1/2013 | Fitz et al. |
| 2013/0018380 A1 | 1/2013 | Fitz et al. |
| 2013/0018464 A1 | 1/2013 | Fitz et al. |
| 2013/0023884 A1 | 1/2013 | Fitz et al. |
| 2013/0024000 A1 | 1/2013 | Bojarski et al. |
| 2013/0030419 A1 | 1/2013 | Fitz et al. |
| 2013/0030441 A1 | 1/2013 | Fitz et al. |
| 2013/0079781 A1 | 3/2013 | Fitz et al. |
| 2013/0079876 A1 | 3/2013 | Fitz et al. |
| 2013/0081247 A1 | 4/2013 | Fitz et al. |
| 2013/0096562 A1 | 4/2013 | Fitz et al. |
| 2013/0103363 A1 | 4/2013 | Lang et al. |
| 2013/0110471 A1 | 5/2013 | Lang et al. |
| 2013/0123792 A1 | 5/2013 | Fitz et al. |
| 2013/0184713 A1 | 7/2013 | Bojarski et al. |

(56) References Cited

U.S. PATENT DOCUMENTS

| | | | |
|---|---|---|---|
| 2013/0197870 A1 | 8/2013 | Steines et al. | |
| 2013/0211409 A1 | 8/2013 | Burdulis, Jr. et al. | |
| 2013/0211410 A1 | 8/2013 | Landes et al. | |
| 2013/0211531 A1* | 8/2013 | Steines | A61F 2/4684 623/20.35 |
| 2013/0245803 A1 | 9/2013 | Lang | |
| 2013/0253522 A1 | 9/2013 | Bojarski et al. | |
| 2013/0289570 A1 | 10/2013 | Chao | |
| 2013/0296874 A1 | 11/2013 | Chao | |
| 2013/0297031 A1 | 11/2013 | Hafez | |
| 2013/0317511 A1 | 11/2013 | Bojarski et al. | |
| 2013/0331850 A1 | 12/2013 | Bojarski et al. | |
| 2014/0005792 A1 | 1/2014 | Lang et al. | |
| 2014/0029814 A1 | 1/2014 | Fitz et al. | |
| 2014/0031826 A1 | 1/2014 | Bojarski et al. | |
| 2014/0039631 A1 | 2/2014 | Bojarski et al. | |
| 2014/0058396 A1 | 2/2014 | Fitz et al. | |
| 2014/0058397 A1 | 2/2014 | Fitz et al. | |
| 2014/0066935 A1 | 3/2014 | Fitz et al. | |
| 2014/0066936 A1 | 3/2014 | Fitz et al. | |
| 2014/0074441 A1 | 3/2014 | Fitz et al. | |
| 2014/0086780 A1 | 3/2014 | Miller et al. | |
| 2014/0142643 A1* | 5/2014 | Bake | A61B 17/1764 606/86 R |
| 2014/0228860 A1* | 8/2014 | Steines | A61F 2/30942 606/130 |

FOREIGN PATENT DOCUMENTS

| | | |
|---|---|---|
| AU | 2005309692 A1 | 6/2006 |
| AU | 2005311558 A1 | 6/2006 |
| AU | 2002310193 B2 | 3/2007 |
| AU | 2006297137 A1 | 4/2007 |
| AU | 2002310193 B8 | 5/2007 |
| AU | 2007202573 A1 | 6/2007 |
| AU | 2007212033 A1 | 8/2007 |
| AU | 2007226924 A1 | 9/2007 |
| AU | 2009221773 A1 | 9/2009 |
| AU | 2009246474 A1 | 11/2009 |
| AU | 2010201200 A1 | 4/2010 |
| AU | 2011203237 A1 | 7/2011 |
| AU | 2010217903 A1 | 9/2011 |
| AU | 2010236263 A1 | 11/2011 |
| AU | 2010264466 A1 | 2/2012 |
| AU | 2010289706 A1 | 3/2012 |
| AU | 2010315099 A1 | 5/2012 |
| AU | 2010327987 A1 | 6/2012 |
| AU | 2011203237 B2 | 10/2012 |
| AU | 2012216829 A1 | 10/2012 |
| AU | 2012217654 A1 | 10/2013 |
| AU | 2007212033 B2 | 1/2014 |
| AU | 2014200073 A1 | 1/2014 |
| AU | 2012289973 A1 | 3/2014 |
| AU | 2012296556 A1 | 3/2014 |
| CA | 2501041 | 4/2004 |
| CA | 2505371 A1 | 5/2004 |
| CA | 2505419 A1 | 6/2004 |
| CA | 2506849 A1 | 6/2004 |
| CA | 2546958 A1 | 6/2005 |
| CA | 2546965 A1 | 6/2005 |
| CA | 2804883 A1 | 6/2005 |
| CA | 2588907 A1 | 6/2006 |
| CA | 2590534 A1 | 6/2006 |
| CA | 2623834 A1 | 4/2007 |
| CA | 2641241 A1 | 8/2007 |
| CA | 2646288 A1 | 9/2007 |
| CA | 2717760 A1 | 9/2009 |
| CA | 2765499 A1 | 12/2010 |
| CA | 2771573 A1 | 3/2011 |
| CA | 2779283 A1 | 5/2011 |
| CA | 2782137 A1 | 6/2011 |
| CA | 2546965 C | 3/2013 |
| CN | 1728976 A | 2/2006 |
| CN | 1729483 A | 2/2006 |
| CN | 1729484 A | 2/2006 |
| CN | 1913844 A | 2/2007 |
| CN | 101111197 A | 1/2008 |
| CN | 101384230 A | 3/2009 |
| CN | 101442960 A | 5/2009 |
| CN | 100502808 C | 6/2009 |
| CN | 102006841 A | 4/2011 |
| CN | 102125448 A | 7/2011 |
| CN | 102405032 A | 4/2012 |
| CN | 102448394 A | 5/2012 |
| CN | 101420911 B | 7/2012 |
| CN | 102599960 A | 7/2012 |
| CN | 1913844 B | 9/2012 |
| CN | 102711670 A | 10/2012 |
| CN | 102724934 A | 10/2012 |
| CN | 102805677 A | 12/2012 |
| CN | 1729483 B | 10/2013 |
| CN | 103476363 A | 12/2013 |
| DE | 60336002 D1 | 3/2011 |
| DE | 60239674 D1 | 5/2011 |
| DE | 602004032166 D1 | 5/2011 |
| DE | 602005027391 D1 | 5/2011 |
| EP | 1555962 A1 | 7/2005 |
| EP | 1558181 A1 | 8/2005 |
| EP | 1567985 A2 | 8/2005 |
| EP | 1575460 A2 | 9/2005 |
| EP | 1686930 A1 | 8/2006 |
| EP | 1686931 A1 | 8/2006 |
| EP | 1389980 A4 | 4/2007 |
| EP | 1814491 A1 | 8/2007 |
| EP | 1833387 A1 | 9/2007 |
| EP | 1686930 A4 | 10/2007 |
| EP | 1686931 A4 | 1/2008 |
| EP | 1928359 A2 | 6/2008 |
| EP | 1951136 A1 | 8/2008 |
| EP | 1981409 A2 | 10/2008 |
| EP | 1996121 A2 | 12/2008 |
| EP | 2114312 A2 | 11/2009 |
| EP | 2124764 A1 | 12/2009 |
| EP | 1928359 A4 | 10/2010 |
| EP | 2259753 A1 | 12/2010 |
| EP | 2265199 A1 | 12/2010 |
| EP | 1555962 B1 | 2/2011 |
| EP | 2292188 A2 | 3/2011 |
| EP | 2292189 A2 | 3/2011 |
| EP | 1389980 B1 | 4/2011 |
| EP | 1686930 B1 | 4/2011 |
| EP | 1833387 B1 | 4/2011 |
| EP | 2303193 A1 | 4/2011 |
| EP | 2316357 A1 | 5/2011 |
| EP | 2324799 A2 | 5/2011 |
| EP | 2335654 A1 | 6/2011 |
| EP | 2403434 A1 | 1/2012 |
| EP | 2405865 A2 | 1/2012 |
| EP | 2419035 A1 | 2/2012 |
| EP | 2265199 A4 | 3/2012 |
| EP | 2303193 A4 | 3/2012 |
| EP | 2259753 A4 | 4/2012 |
| EP | 2292188 A3 | 5/2012 |
| EP | 2292189 A3 | 5/2012 |
| EP | 2445451 A1 | 5/2012 |
| EP | 2470126 A1 | 7/2012 |
| EP | 2496183 A2 | 9/2012 |
| EP | 2509539 A2 | 10/2012 |
| EP | 2512381 A2 | 10/2012 |
| EP | 2324799 A3 | 1/2013 |
| EP | 2419035 A4 | 1/2013 |
| EP | 2445451 A4 | 3/2013 |
| EP | 2564792 A1 | 3/2013 |
| EP | 2403434 A4 | 4/2013 |
| EP | 2591756 A1 | 5/2013 |
| EP | 2496183 A4 | 12/2013 |
| EP | 2512381 A4 | 12/2013 |
| EP | 2649951 A2 | 12/2013 |
| EP | 2649951 A3 | 12/2013 |
| EP | 2671520 A3 | 12/2013 |
| EP | 2671521 A3 | 12/2013 |
| EP | 2671522 A3 | 12/2013 |
| EP | 2114312 B1 | 1/2014 |

(56) References Cited

FOREIGN PATENT DOCUMENTS

| | | | |
|---|---|---|---|
| EP | 2710967 | A2 | 3/2014 |
| GB | 2484042 | A | 3/2012 |
| GB | 2489884 | A | 10/2012 |
| GB | 201213674 | | 10/2012 |
| GB | 2484042 | B | 3/2014 |
| HK | 1059882 | A1 | 8/2011 |
| HK | 1072710 | A1 | 8/2011 |
| HK | 1087324 | A1 | 11/2011 |
| HK | 1104776 | A1 | 11/2011 |
| JP | 2006510403 | A | 3/2006 |
| JP | 2007514470 | A | 6/2007 |
| JP | 2011519713 | A | 7/2011 |
| JP | 2011224384 | A | 11/2011 |
| JP | 2012091033 | A | 5/2012 |
| JP | 2012176318 | A | 9/2012 |
| JP | 5053515 | B2 | 10/2012 |
| JP | 2012187415 | A | 10/2012 |
| JP | 2012523897 | A | 10/2012 |
| JP | 5074036 | B2 | 11/2012 |
| JP | 2012531265 | A | 12/2012 |
| JP | 2013503007 | A | 1/2013 |
| JP | 5148284 | B2 | 2/2013 |
| JP | 5198069 | B2 | 5/2013 |
| JP | 2014000425 | A | 1/2014 |
| KR | 20050072500 | A | 7/2005 |
| KR | 20050084024 | A | 8/2005 |
| KR | 20120090997 | A | 8/2012 |
| KR | 20120102576 | A | 9/2012 |
| MX | 2012007140 | A | 1/2013 |
| NZ | 597261 | A | 11/2013 |
| SG | 173840 | A1 | 9/2011 |
| SG | 175229 | A1 | 11/2011 |
| SG | 176833 | A1 | 1/2012 |
| SG | 178836 | A1 | 4/2012 |
| SG | 193484 | A1 | 10/2013 |
| TW | 200509870 | A | 3/2005 |
| TW | 1231755 | B | 5/2005 |
| TW | 200800123 | A | 1/2008 |
| TW | 1330075 | B | 9/2010 |
| WO | 2004049981 | A3 | 6/2004 |
| WO | 2004051301 | A3 | 6/2004 |
| WO | 2005051239 | A1 | 6/2005 |
| WO | 2005051240 | A1 | 6/2005 |
| WO | 2006058057 | A2 | 6/2006 |
| WO | 2006060795 | A1 | 6/2006 |
| WO | 2006058057 | A8 | 7/2006 |
| WO | 2007041375 | A2 | 4/2007 |
| WO | 2007062103 | A1 | 5/2007 |
| WO | 2007092841 | A2 | 8/2007 |
| WO | 2007109641 | A2 | 9/2007 |
| WO | 2007092841 | A3 | 11/2007 |
| WO | 2007109641 | A3 | 12/2007 |
| WO | 2008101090 | A2 | 8/2008 |
| WO | 2008112996 | A1 | 9/2008 |
| WO | 2008101090 | A3 | 11/2008 |
| WO | 2008157412 | A2 | 12/2008 |
| WO | 2007041375 | A3 | 4/2009 |
| WO | 2008157412 | A3 | 4/2009 |
| WO | 2009111626 | A2 | 9/2009 |
| WO | 2009111639 | A1 | 9/2009 |
| WO | 2009111656 | A1 | 9/2009 |
| WO | 2009140294 | A1 | 11/2009 |
| WO | 2009154691 | A2 | 12/2009 |
| WO | 2009111626 | A3 | 1/2010 |
| WO | 2010099231 | A2 | 9/2010 |
| WO | 2010099353 | A1 | 9/2010 |
| WO | 2010121147 | A1 | 10/2010 |
| WO | 2010099231 | A3 | 11/2010 |
| WO | 2011008968 | A1 | 1/2011 |
| WO | 2011028624 | A1 | 3/2011 |
| WO | 2011056995 | A2 | 5/2011 |
| WO | 2011072235 | A2 | 6/2011 |
| WO | 2011075697 | A2 | 6/2011 |
| WO | 2011056995 | A3 | 9/2011 |
| WO | 2011075697 | A3 | 10/2011 |
| WO | 2011072235 | A3 | 12/2011 |
| WO | 2011156748 | A2 | 12/2011 |
| WO | 2012112694 | A1 | 8/2012 |
| WO | 2012112694 | A2 | 8/2012 |
| WO | 2012112698 | A2 | 8/2012 |
| WO | 2012112701 | A2 | 8/2012 |
| WO | 2012112702 | A2 | 8/2012 |
| WO | 2012112694 | A3 | 1/2013 |
| WO | 2012112701 | A3 | 1/2013 |
| WO | 2012112702 | A3 | 1/2013 |
| WO | 2013020026 | A1 | 2/2013 |
| WO | 2013025814 | A1 | 2/2013 |
| WO | 2012112698 | A3 | 3/2013 |
| WO | 2013056036 | A1 | 4/2013 |
| WO | 2013119790 | A1 | 8/2013 |
| WO | 2013119865 | A1 | 8/2013 |
| WO | 2013131066 | A1 | 9/2013 |
| WO | 2013152341 | A1 | 10/2013 |
| WO | 2013155500 | A1 | 10/2013 |
| WO | 2013155501 | A1 | 10/2013 |
| WO | 2014008444 | A1 | 1/2014 |
| WO | 2014035991 | A1 | 3/2014 |
| WO | 2014047514 | A1 | 3/2014 |

OTHER PUBLICATIONS

Hofmann et al, "Natural-Knee II System", Intermedics Orthopedics, Austin, TX, 1995.

* cited by examiner

METHOD AND SYSTEM FOR CREATING PATIENT-SPECIFIC INSTRUMENTATION FOR CHONDRAL GRAFT TRANSFER

CROSS-REFERENCE TO RELATED APPLICATION

The present application claims priority on U.S. Provisional Patent Application No. 61/590,157, incorporated herewith by reference.

FIELD OF THE APPLICATION

The present application relates to chondral graft transfer, and more particularly to a method and system for the creation of patient-specific instrumentation for performing chondral graft transfer, for instance in an osteoarticular transfer procedure for the knee.

BACKGROUND OF THE ART

In pre-knee replacement treatment for arthritis, cartilage replacement is often used on some patients (e.g., younger active patients) as a stopgap measure to delay the need for a complete total knee arthroplasty (a.k.a, total knee replacement). There are numerous possible treatments involving replacement of the cartilage with autografts or with allografts.

One such autograft treatment is the osteoarticular transfer, referred to as OATS, designed to remove cartilage from one area and graft it onto another. One consideration in such treatment is the need to match both cartilage thickness and curvature between donor location and graft location, to ensure an optimal graft. Indeed, with improper graft shapes, there may result some difficulties in aligning the hyaline cartilage in thickness and/or curvature.

SUMMARY OF THE APPLICATION

It is therefore an aim of the present disclosure to provide a novel method and system to create patient-specific instrumentation to perform chondral graft transfer.

Therefore, in accordance with a first embodiment of the present application, there is provided a method for creating at least one patient-specific instrument model for chondral graft removal, comprising: determining a graft geometry from a defect region in a bone/cartilage model of an articular region of a bone; identifying at least one donor location from the bone/cartilage model, using the graft geometry; and creating a model of at least one graft-removal patient-specific instrument using the at least one donor location, the graft geometry, and the bone/cartilage model, the graft-removal patient-specific instrument model comprising a bone/cartilage interface surface shaped as a function of the bone/cartilage model for the at least one graft-removal patient-specific instrument to be selectively positioned on the bone/cartilage to remove cartilage from the at least one donor location.

Further in accordance with a second embodiment of the present disclosure, there is provided a system for creating a patient-specific instrument model for chondral graft plugging, comprising: a bone model generator for producing a bone/cartilage model of an articular region of a bone from images thereof; a defect geometry identifier for identifying a graft geometry from a defect region of said bone/cartilage model; a donor locator for locating an autograft at at least one donor site or identifying an allograft from a database, using said bone/cartilage model and the graft geometry; and a patient-specific instrument model generator for creating a model of a graft-plugging patient-specific instrument from said bone/cartilage model, and the graft geometry, the graft-plugging patient-specific instrument model comprising a bone/cartilage interface surface shaped as a function of the bone/cartilage model for the at least one graft-plugging patient-specific instrument to be selectively positioned on the bone/cartilage to pose at least one of the autograft and the allograft at the defect region.

Still further in accordance with a third embodiment of the present disclosure, there is provided a method for creating at least one patient-specific instrument model for chondral graft plugging, comprising: determining a graft geometry from a defect region in a bone/cartilage model of an articular region of a bone; identifying at least one of a corresponding allograft and autograft with a donor location from the bone/cartilage model, using the graft geometry; and creating a model of at least one graft-plugging patient-specific instrument using the graft geometry, and the bone/cartilage model, the at least one graft-plugging patient-specific instrument adapted to plug at least one of an autograft and an allograft at the defect region.

DESCRIPTION OF THE PREFERRED EMBODIMENTS

Figure 1:
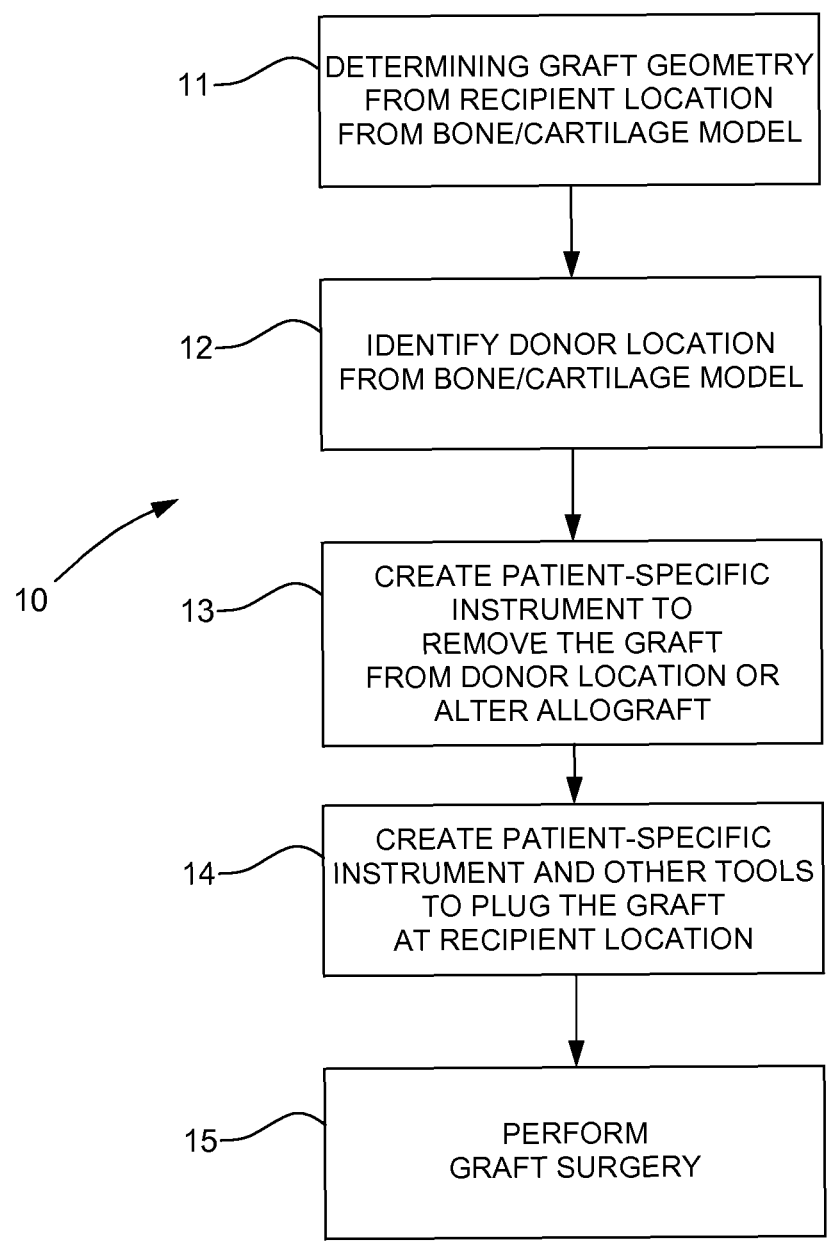
FIG. 1 is a flow chart of a method for creating patient-specific instrumentation for osteoarticular transfer surgery in accordance with the present disclosure.

Referring to the drawings, and more particularly to FIG. 1, there is illustrated at 10 a method for performing osteoarticular transfer surgery, for instance in knee applications. The method 10 creates and uses patient-specific instrumentation (hereinafter "PSI") to remove and/or graft cartilage.

According to 11, the graft geometry is determined from the recipient location, i.e., the chondral articular area requiring the graft. The graft geometry may comprise the dimensions of the required graft, the thickness of the required graft, and the curvature. The graft geometry may be identified by a preoperative step, with non-invasive or minimally invasive techniques being well suited for 11. For instance, imaging technologies such as magnetic-resonance imagery or contrast-enhanced computed tomography of the bone are two of numerous technologies that can used to image chondral defects, by the imaging of bone and chondral tissue. Other methods are contemplated as well.

With the imaging, the chondral defect may be quantified with the geometric details set forth above. Moreover, data is obtained pertaining to the global geometry of the bone and cartilage. The data is used to create a model of an operated site portion of the bone and cartilage including that of an area surrounding the recipient location. Reference will be made hereinafter to the model obtained in 11 as the bone/cartilage model. This will refer to a model of a portion of a bone, with layers thereon distinguishing bone from cartilage.

According to 12, the model of the operated site portion is used to identify donor location. The donor location comprises cartilage that generally matches the geometric details of the required graft. Moreover, the donor location is selected for practical considerations, for instance to minimize post-surgery impact on articular integrity. The donor location may consist of numerous donor sublocations, to create a graft mosaic from cartilage sections that matches the geometry details of the required draft.

According to an embodiment, the graft geometry may match that of available allografts. The graft geometry may therefore be compared to geometries in a database of allografts to determine whether an allograft could be used instead of or in addition to an autograft. The comparison between the modeled graft geometry and the allograft geometry could find compatibility between geometries despite some deviations. Moreover, the allograft database may comprise allografts harvested from surfaces other than that matching the donor site. For example, if appropriate and if geometries match, allografts from shoulder, hip, ankle, and the like could be used for the tibial plateau, etc.

According to 13, PSI is created to remove a graft from the donor location, or to alter an allograft. An example of PSI is provided and detailed hereinafter. The PSI is manufactured specifically for the patient, using the model obtained from the imaging in 11, as well as graft geometry and donor location or sublocations. For autograft removal applications, the PSI has a geometry that is made for precisely and accurately engaging onto the bone and cartilage of the patient for the removal of the graft or graft portions from the donor location or sublocations.

According to 14, PSI may be created to plug the graft obtained from the donor location in the recipient location. Again, the PSI is manufactured specifically for the patient, using the model obtained from the imaging in step 11, as well as recipient location. The PSI has a geometry that is made for precisely and accurately engaging onto the bone and cartilage of the patient for plugging the graft or graft portions at the recipient location. The PSI according to 14 may be used to plug an allograft in the donor location.

Other PSI may be created to perform other tasks. For instance, an instrument could be used to clean (e.g., burr) chondral tissue in the defect region with a view to receiving the graft. The PSI used for such purpose may include a support to hold the appropriate tools in a specific position and/or orientation relative to the tool, to control the cleaning procedure. PSI could be generated to modify allografts as well.

According to 15, graft surgery (i.e., osteoarticular transfer) is performed. Accordingly, steps 11-14 may be performed pre-operatively using proper imaging technologies, to minimize surgical time. Moreover, by the use of PSI, the surgical procedure is performed efficiently, as the PSI is already shaped to the bone model, whereby no extensive calibration is required.

Figure 2:
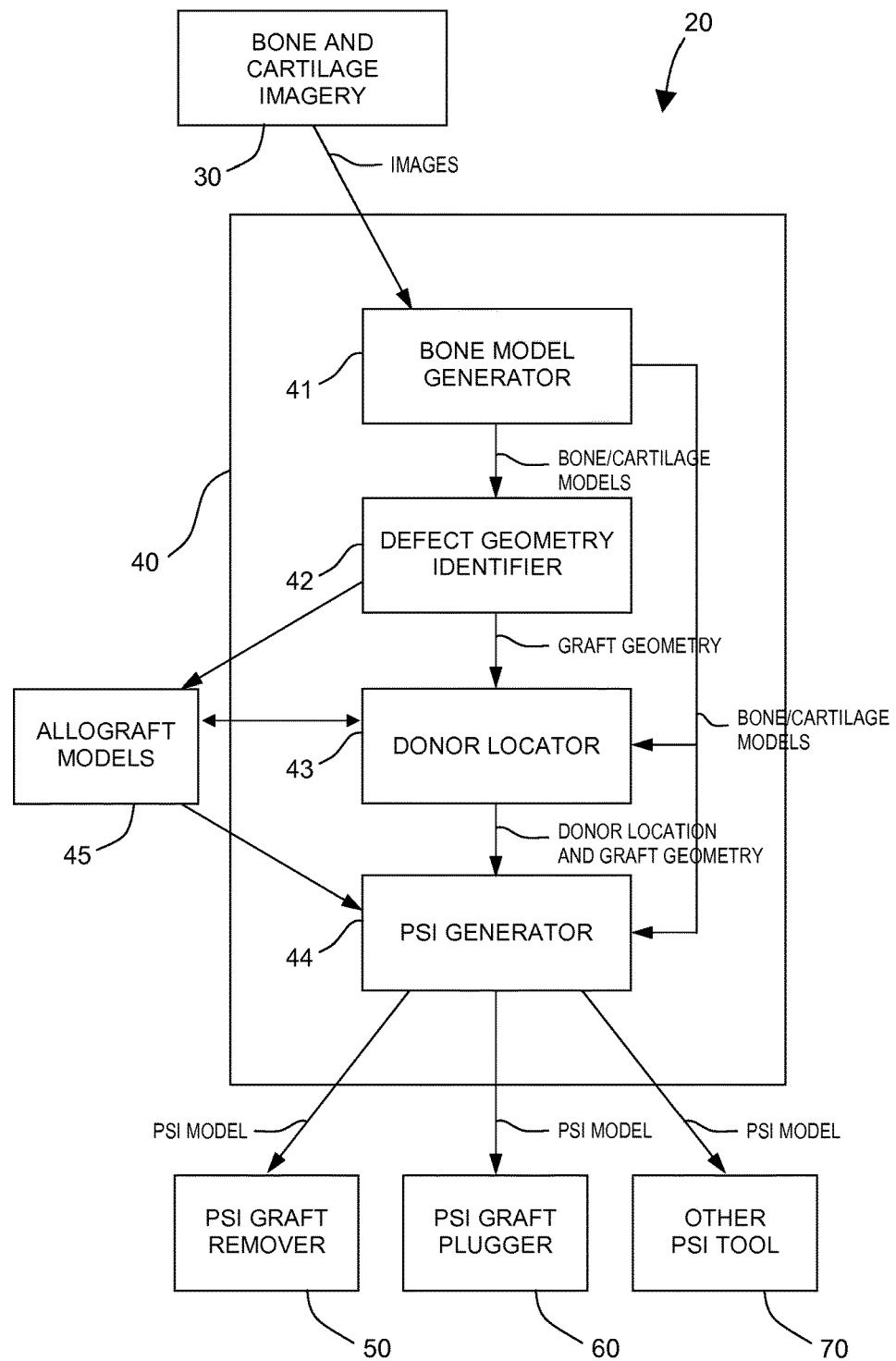
FIG. 2 is a block diagram of a patient-specific instrumentation computer-assisted surgery system for osteoarticular transfer in accordance with the present disclosure.

Referring to FIG. 2, a computer-assisted surgery system (hereinafter "CAS system") for osteoarticular transfer is generally shown at 20. The CAS system 20 receives bone and cartilage imagery 30 from any appropriate imaging technology (e.g., MRI, enhanced-contrast CT). The imaging technology apparatus may be a part of the CAS system 20. The imagery 30 may comprise three-dimensional images of the articular region of the bone, with layers representative of the cartilage thereon, enabling to discriminate bone from cartilage.

The CAS system 20 comprises a CAS processor unit 40 that receives the bone images 30, and that will produce PSI models from the images 30. The CAS processor unit 40 has a processor to run the application that will generate the PSI models. Accordingly, the CAS processor unit 40 may be any appropriate computer or processing unit. User interfaces (e.g., monitor, screen, keyboard, mouse, touch-screen) are part of the CAS processor unit 40, for the involvement of an operator in the creation of the PSI models.

The CAS processor unit 40 comprises a bone model generator 41. The bone model generator 41 is used to interpret the images 30, and thus to create a model of the articular region of the bone. The model distinguishes chondral tissue from the bone, thereby enabling to segment out the chondral tissue from the bone, effectively creating a model of the cartilage on its supporting structure, i.e., the bone. The operator's input may be required in distinguishing cartilage from bone and/or for confirming the proper segmentation between bone and cartilage. The interfaces may be used for this purpose.

A defect geometry identifier 42 uses the model of the cartilage to determine a graft geometry. The defect geometry identifier 42 defines the geometrical parameters of the graft, such as dimensions, thickness, curvature, etc. The operator's input may also be required, for instance to delimit chondral defect from the images.

A donor locator 43 then matches the graft geometry from the defect geometry identifier 42 to the cartilage model of the bone model generator 41. The donor locator 43 locates parts of the cartilage model that could be donor locations or sites, from the geometric data of the required graft. The donor locator 43 may also ensure that the donor site is indeed well suited for the removal of graft, without affecting the articular integrity. For instance, the donor locator 43 may relate the donor site to its location on the bone, with some regions of the bone being excluded from being donor sites.

The donor locator 43 may identify more than one potential donor location, with the operator selecting the donor location among the potential sites. Moreover, the donor locator 43 may identify a plurality of donor sublocations, which sublocations would produce a graft mosaic having the geometry of the defect, i.e., the graft geometry provided by the defect geometry identifier 42.

Still referring to FIG. 2, a PSI generator 44 uses the graft geometry, donor locations and bone/cartilage models to produce PSI models. The PSI models will be used to manufacture patient-specific instrumentation that will be used to remove specific sizes and geometries of chondral tissue from the donor locations, that may be used to plug chondral defect, and that may be used to clean a defect zone with a view to receiving a graft. As seen hereinafter, the PSI must connect in a precise and accurate way to the bone/cartilage, whereby the PSI generator 44 uses the bone/cartilage models to produce the PSI models. The PSI models may be in any appropriate format to allow the manufacture of PSI. For instance, the PSI models are formatted into NC machine files, technical data, visual or digital models, etc.

As mentioned above, the graft geometry may be compared with the geometries of available allografts by the donor locator 43, as shown by 45. If a match is found, an allograft or allografts could be used instead or in addition to autografts. A PSI model or models may be produced for PSI that may alter an allograft or allografts into the graft having an appropriate geometry for the recipient location.

Figure 3:
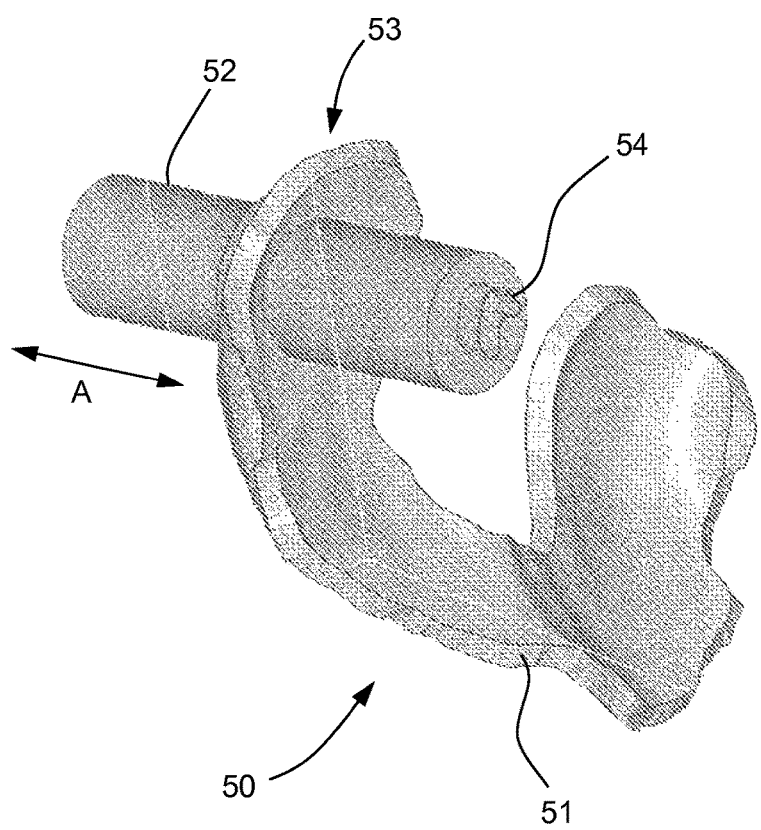
FIG. 3 is a perspective view of a patient-specific instrumentation graft remover in accordance with the present disclosure.

Referring concurrently to FIGS. 2 and 3, an example of a PSI graft remover 50 is shown, the graft remover 50 having a similar configuration to a PSI graft plugger 60 (FIG. 2). The PSI graft remover 50 comprises a guide 51. The guide 51 is an arcuate plate or like PSI interface that is specifically shaped to geometrically correspond to a surface of the bone and/or cartilage surrounding the donor location, or recipient location in the case of the PSI graft plugger 60. Accordingly, when the guide 51 is applied against the bone/cartilage, a bone/cartilage interface surface thereof will be in flush contact with a surface of bone and/or cartilage adjacent to the donor location and/or the recipient location and therefore in a desired position and orientation relative to the bone/cartilage. Moreover, although the interface surface 51 is shown as being a single relatively large surface, the interface surface 51 may defined by the end surfaces of a plurality of posts that are modeled as a function of a geometry of the bone/cartilage.

The guide 51 may have an opening slidingly supporting a punch 52, thereby forming a sliding or translational joint 53. According to an embodiment, the translation joint 53 is a prismatic joint, or any appropriate joint that limits the movement of the punch 52 to one degree of freedom (DOF). As another example, a one-DOF pivot joint could relate the punch to the guide. In FIG. 3, the guide 51 moves along direction A. It is also considered that the guide 51 and tooling be in a fixed relation to one another, i.e., without any joint providing any DOF therebetween.

The PSI graft remover 50, the PSI graft plugger 60 and other PSI tools 70 have a tooling end at which a tool is located, for performing alterations on cartilage. In FIG. 3, the tool is a cutout 54 is located at the tooling end of the punch 52, in a predetermined position and orientation relative to the interface surface of the guide 51, to perform alterations at the donor location. The periphery of the cutout 54 (i.e., cutter) is selected as a function of the graft geometry, with the free edge of the cutout 54 being sharpened to cut through chondral tissue with a suitable force applied onto the punch 52. Moreover, the height of the cutout 57 may be defined so as to remove a desired thickness and geometry of cartilage. Therefore, the PSI graft remover 50 is specifically devised to cut out tightly controlled cartilage shapes. A tool with a geometry similar to the cutout 54 may be used in the PSI graft plugger 60 to releasably support graft during its plugging, in the case where the PSI graft plugger 60 has a configuration similar to that of the PSI graft remover 50. In such a case, the cutout-like tool is in a predetermined position and orientation relative to the interface surface of the guide 51, to pose the graft at the recipient location. As an alternative, the plugger 60 may have any appropriate configurations to releasably hold the graft in the desired position and orientation on the guide 51.

Referring to FIG. 2, other similar PSI tools may be devised for other functions, such as graft plugging with a PSI graft plugger 60, other any other appropriate function via tools 70 (e.g. burring). Such other tools would have appropriate geometries to interact with the bone and cartilage. The other tools may be designed as a function of any one of the bone and cartilage models, donor location, graft geometry, recipient location, etc.

The invention claimed is:

1. A method for creating at least one patient-specific instrument model for chondral graft removal, comprising:
   determining with a computer-assisted surgery processor unit a graft geometry from a defect region in a bone and cartilage digital model of an articular region of a bone, the graft geometry having a non-circular periphery corresponding to a defect in cartilage;
   identifying with the computer-assisted surgery processor unit at least one donor location from the bone and cartilage digital model, using the graft geometry;
   creating with the computer-assisted surgery processor unit a digital model of at least one graft-removal patient-specific instrument using the at least one donor location, the graft geometry, and the bone and cartilage digital model, the graft-removal patient-specific instrument model comprising an interface surface shaped as a function of the bone and cartilage digital model for the at least one graft-removal patient-specific instrument to be selectively positioned on at least one of the bone and cartilage to remove cartilage from the at least one donor location, and a tooling end having a cutout with a geometry corresponding to the graft geometry for removing the cartilage with said graft geometry, the cutout having said non-circular periphery to match the defect; and
   outputting with the computer-assisted surgery processor unit the digital model of the at least one graft-removal patient-specific instrument as a digital fabrication file.

2. The method according to claim 1, wherein creating the digital model of the at least one graft-removal patient-specific instrument comprises creating a translational joint between the interface surface and the tooling end for guiding the tooling end toward the donor location.

3. The method according to claim 1, further comprising creating a digital model of a graft-plugging patient-specific instrument adapted to plug the defect region with at least one graft, using the bone and cartilage digital model of the articular region of the bone and the graft geometry, the graft-plugging patient-specific instrument digital model comprising another interface surface shaped as a function of the bone and cartilage model for the at least one graft-plugging patient-specific instrument to be selectively positioned on at least one of the bone and cartilage to plug a graft at the defect region.

4. The method according to claim 3, wherein creating the digital model of the at least one graft-plugging patient-specific instrument comprises creating the other interface surface for contacting the bone, and a tooling end positioned relative to the other interface surface for plugging the graft at the defect region.

5. The method according to claim 4, wherein creating the digital model of the at least one graft-plugging patient-specific instrument comprises creating a translational joint between the other interface surface and the tooling end for guiding the tooling end in plugging the graft at the defect region.

6. The method according to claim 3, wherein:
   the other interface surface is distinct from the interface surface, and
   the other interface surface corresponds to a single surface of the at least one patient-specific instrument that is configured to be in flush contact with a surface of tissue adjacent to the defect region.

7. The method according to claim 3, wherein creating the digital model of the at least one graft-removal patient-specific instrument comprises:
   creating, with the computer-assisted surgery processor unit, the interface surface of the digital model of the at least one graft-removal patient-specific instrument; and
   creating, with the computer-assisted surgery processor unit, the tooling end of the digital model of the at least one graft-removal patient-specific instrument.

8. The method according to claim 1, further comprising creating the bone and cartilage digital model from imaging of the bone and cartilage.

9. The method according to claim 1, wherein the method is performed pre-operatively.

10. The method according to claim 1, further comprising manufacturing the at least one graft-removal patient-specific instrument specifically for a patient using the digital fabrication file.

11. The method according to claim 1, wherein:
the interface surface is shaped as a function of a portion of the bone and cartilage digital model that corresponds to the at least one donor location; and
the interface surface corresponds to a single surface of the at least one patient-specific instrument that is configured to be in flush contact with a surface of tissue adjacent to the at least one donor location.

12. The method according to claim 11, wherein the interface surface is shaped to position and orientation the at least one graft-removal patient-specific instrument in a desired position and orientation relative to the at least one donor location.

13. A system for creating a patient-specific instrument model for chondral graft plugging, the system including a computer-assisted surgery processor unit comprising:
a bone model generator for producing a bone and cartilage digital model of an articular region of a bone from images thereof;
a defect geometry identifier for identifying a graft geometry from a defect region of said bone and cartilage digital model, the graft geometry having a non-circular periphery corresponding to a defect in cartilage;
a donor locator for locating an autograft in at least one donor site or identifying an allograft from a database, using said bone and cartilage digital model and the graft geometry; and
a patient-specific instrument model generator for creating a digital model of a graft-plugging patient-specific instrument from said bone and cartilage digital model, and the graft geometry, the graft-plugging patient-specific instrument digital model comprising an interface surface shaped as a function of the bone and cartilage digital model for the at least one graft-plugging patient-specific instrument to be selectively positioned on at least one of the bone and cartilage to plug at least one of the autograft and the allograft at the defect region, a tooling end having a periphery to attach to the non-circular periphery of the defect and positioned relative to the interface surface for plugging at least one of the autograft and allograft at the defect region, and a translational joint between the interface surface and the tool for guiding the tool in plugging the graft at the defect region.

14. The system according to claim 13, wherein the patient-specific instrument model generator creates a model of a graft-removal patient-specific instrument from said bone and cartilage model, the donor site and the graft geometry, the graft-removal patient-specific instrument model comprising another interface surface shaped as a function of the bone and cartilage digital model for the at least one graft-removal patient-specific instrument to be selectively positioned on at least one of the bone and cartilage to remove the autograft from the at least one donor location.

15. The system according to claim 14, wherein the patient-specific instrument model generator creates the other interface surface of the graft-removal patient-specific instrument model for contacting at least one of the bone and cartilage, and a tooling end positioned relative to the interface surface for removing the autograft at the donor location, the tooling end having a cutout with a geometry corresponding to the graft geometry for removing the cartilage with said graft geometry, the cutout having said non-circular periphery to match the defect.

16. The system according to claim 15, wherein the patient-specific instrument model generator creates a translational joint in graft-removal patient-specific instrument model between other interface surface and the tool for guiding the tool toward the donor location.

17. A method for creating at least one patient-specific instrument model for chondral graft plugging, comprising:
determining with a computer-assisted surgery processor unit a graft geometry from a defect region in a bone and cartilage digital model of an articular region of a bone, the graft geometry having a non-circular periphery corresponding to a defect in cartilage;
identifying with the computer-assisted surgery processor unit at least one of a corresponding allograft and autograft with a donor location from the bone and cartilage digital model, using the graft geometry;
creating with the computer-assisted surgery processor unit a digital model of at least one graft-plugging patient-specific instrument using the graft geometry, and the bone and cartilage digital model, the at least one graft-plugging patient-specific instrument adapted to plug at least one of an autograft and an allograft at the defect region, the graft-plugging patient-specific instrument digital model comprising an interface surface shaped as a function of the bone and cartilage digital model for the at least one graft-plugging patient-specific instrument to be selectively positioned on at least one of the bone and cartilage to plug at least one of the autograft and allograft at the defect region, a tooling end having a periphery to attach to the non-circular periphery of the defect and positioned relative to the interface surface for plugging at least one of the autograft and allograft at the defect region, and a translational joint between the interface surface and the tool for guiding the tool in plugging the graft at the defect region; and
outputting with the computer-assisted surgery processor unit the digital model of the at least one graft-plugging patient-specific instrument as a digital fabrication file.

18. The method according to claim 17, further comprising creating the bone and cartilage digital model from imaging of the bone and cartilage.

19. The method according to claim 17, wherein the method is performed pre-operatively.

20. The method according to claim 17, further comprising manufacturing the at least one graft-plugging patient-specific instrument specifically for a patient using the digital fabrication file.

* * * * *